United States Patent
Park et al.

(10) Patent No.: US 8,493,561 B2
(45) Date of Patent: Jul. 23, 2013

(54) DEVICE FOR ON-SITE MEASUREMENT OF CONCENTRATION OF URANIUM IN HIGH TEMPERATURE MOLTEN SALTS

(75) Inventors: Yong Joon Park, Daejeon (KR); Sang Eun Bae, Gimcheon (KR); Young-Hwan Cho, Daejeon (KR); Kyuseok Song, Daejeon (KR)

(73) Assignees: Korea Atomic Energy Research Institute, Daejeon (KR); Korea Hydro & Nuclear Power Co., Ltd., Seoul (KR)

( * ) Notice: Subject to any disclaimer, the term of this patent is extended or adjusted under 35 U.S.C. 154(b) by 521 days.

(21) Appl. No.: 12/977,530

(22) Filed: Dec. 23, 2010

(65) Prior Publication Data
US 2012/0026495 A1    Feb. 2, 2012

(30) Foreign Application Priority Data
Jul. 30, 2010   (KR) .............................. 2010-0074109

(51) Int. Cl.
*G01J 3/28* (2006.01)
(52) U.S. Cl.
USPC .......................................... 356/326; 356/436
(58) Field of Classification Search
USPC ................................................ 356/326, 436
See application file for complete search history.

(56) References Cited

U.S. PATENT DOCUMENTS

| | | | | |
|---|---|---|---|---|
| 2,580,500 A | * | 1/1952 | Albert | 356/442 |
| 3,645,628 A | * | 2/1972 | Bojic et al. | 356/326 |
| 3,733,130 A | * | 5/1973 | Young | 356/246 |
| 4,725,148 A | * | 2/1988 | Endo et al. | 356/442 |
| 4,986,658 A | * | 1/1991 | Kim | 356/328 |
| 5,822,072 A | * | 10/1998 | Dai et al. | 356/301 |
| 2003/0174325 A1 | * | 9/2003 | Zhang et al. | 356/318 |

OTHER PUBLICATIONS

Young et al., "Application of Raman Spectroscopy to High-Temperature Analytical Measurements", OSTI, 1998, pp. 1-9.*

* cited by examiner

*Primary Examiner* — Kara E Geisel
(74) *Attorney, Agent, or Firm* — Baker & Hostetler LLP (57) ABSTRACT

A device for on-site measurement of concentration of uranium in high temperature molten salts is provided. More particularly, this device can be directly applied to a pyroprocess for reusing spent nuclear fuel and determine concentration of uranium 3+ and 4+ chemical species using ultraviolet-visible light absorption spectrometry. The device includes first and second optical waveguides submerged in molten salts including uranium through a port formed at an upper side of a pyrochemical process apparatus; a lengthwise driver installed at the port to be operated to adjust a distance between the optical waveguides; a light source for supplying light to the second optical waveguide as any one of the optical waveguides; and a spectrometer connected to the first optical waveguide as the other one of the optical waveguides to analyze the light emitted from the second optical waveguide and introduced through the first optical waveguide via the molten salts.

12 Claims, 5 Drawing Sheets

DEVICE FOR ON-SITE MEASUREMENT OF CONCENTRATION OF URANIUM IN HIGH TEMPERATURE MOLTEN SALTS

CROSS-REFERENCE TO RELATED APPLICATIONS

This application claims priority to foreign Patent Application KR 2010-0074109, filed on Jul. 30, 2010, the disclosure of which is incorporated herein by reference in its entirety.

FIELD OF THE INVENTION

The present invention relates to a device for on-site measurement of concentration of uranium in high temperature molten salts, and more particularly, to a device for on-site measurement of concentration of uranium in high temperature molten salts that can be directly applied to a pyroprocess for reusing spent nuclear fuel and speciation of uranium 3+ and 4+ chemical species using ultraviolet-visible light absorption spectrometry.

BACKGROUND OF THE INVENTION

In recent times, disposal and processing of spent nuclear fuel are becoming an important global issue to be solved for nuclear power plants which are attracting attention as environmentally friendly energy. In Korea, the government has selected a pyrochemical process as a recycling technology of spent nuclear fuel and, in addition to development of related process techniques such as electrolytic reduction, electrolytic refining and electrolytic winning, research and development of molten-salt-related basic technology is being performed.

Molten salts are typically used as solvent for manufacturing aluminum, magnesium, sodium, and so on, metallurgical and electrochemical importance of the molten salts has been recognized from about 40 years ago, and research into molten salts is being actively performed. Molten salts may be generally classified into four kinds, chloride-based salts such as LiCl—KCl, LiCl—NaCl, KCl—LiCl—NaCl, and so on, fluoride-based salts such as LiF—NaF—KF, LiF—NaF, LiF, and so on, cyanide-based salts such as NaCN, KCN, and so on, and an oxygen-containing salts such as $CaC_{l2}$—$CaWO_4$, and so on. In addition, research into bromide-based and iodine-based salts is also being performed.

Such molten salts have the following advantages, which make them very beneficial as an electrolyte. First, these molten salts are electrochemically stable and have high overpotential for decomposition. In addition, these molten salts have high electrical conductivity, and refractor metal which is not electrolytically deposited in an aqueous solution can be electrolytically deposited. Further, flat and thick deposition is also possible.

The spent nuclear fuel is converted into a metal conversion body during the electrolytic reduction process, and moves to an electrolytic refining reactor formed of an anode basket, in which a metal conversion body is contained in a LiCl—KCl high temperature molten salt electrolyte, and a solid cathode, to collect uranium only. When a potential is applied to these electrodes, uranium, rare earth metal and trans uranium (TRU) elements are oxidized and melted at a surface of the anode, and only uranium ions are selectively moved to the cathode to be deposited thereon as a pure uranium metal.

The electrolytic winning process of the pyrochemical process, which is a follow-up process of the electrolytic refining process, is recognized as a very important process in order to perform nuclear non-proliferation, because both uranium and TRU are simultaneously collected using a liquid cadmium cathode (LCC). In operation of the electrolytic refining and winning processes, precise measurement of concentration of uranium existing in the molten salts is very important.

While the conventional art collects molten salts and measures concentration of the molten salts using analysis techniques such as ICP-AES or ICP-MS, real time on-site analysis of uranium is essentially needed to smoothly perform the processes.

The uranium exists as chloride in the molten salts, and mainly has a type of uranium trichloride ($UCl_3$) with an oxidation number of 3+. Since the uranium trichloride molten salts have a thick red wine color whereas uranium tetrachloride ($UCl_4$) with an oxidation number of 4+ has a thin yellowish green color, it will be appreciated that a strong light absorption peak is provided in the visible light region.

Ultraviolet-visible light absorption spectrometry, which is generally used, is a method of quantitatively or qualitatively analyzing concentrations of elements in a sample using the degree to which the sample absorbs ultraviolet or visible light. Light absorbance of a molecule at the ultraviolet and visible light region is relevant to an electron structure of the molecule. A spectrum cell in which a sample is inserted generally uses a quartz cell at an ultraviolet region. When only a peak is observed at the visible light region, a general glass cell may be used. In directly applying absorption spectrometry to the pyrochemical process, in order to employ conventional absorption spectrometry, a quartz window through which ultraviolet-visible light can pass must be provided in a process apparatus. However, corrosion may occur due to a process material such as $Li_2O$, and so on, included in the molten salts, affecting the integrity thereof.

The quantitative analysis using the absorption spectrometry follows Beer's Law (A=ebC), i.e., intensity of light (light absorbance, A) absorbed by a sample is in proportion to concentration (C) of the sample. Here, b represents a width of a spectrum cell in which a sample is contained. When the concentration is too thick, due to a phenomenon in which an absorption peak is saturated, the absorption saturation can be solved by reducing the width of the cell. Accordingly, in order to perform on-site real time analysis of the process material, the width of the spectrum cell must be adjusted according to a concentration range of uranium existing in the molten salts. In addition, since the quartz is likely to be broken due to corrosion by lithium oxide in the molten salts during a long period of operation, the quartz window must be periodically exchanged with a new one.

SUMMARY OF THE INVENTION

In order to solve the problems, embodiments of the present invention advantageously provide a device for on-site measurement of concentration of uranium in high temperature molten salts using ultraviolet-visible light absorption spectrometry capable of quantitatively analyzing concentration of uranium in molten salts in real time in a pyrochemical process.

According to an aspect of the present invention, there is provided a device for on-site measurement of concentration of uranium in high temperature molten salts including: first and second optical waveguides submerged in molten salts including uranium through a port formed at an upper side of a pyrochemical process apparatus; a lengthwise driver installed at the port to be operated to adjust a distance between the optical waveguides; a light source for supplying light to the second optical waveguide as any one of the optical waveguides; and a spectrometer connected to the first optical waveguide as the other one of the optical waveguides to analyze the light emitted from the second optical waveguide and introduced through the first optical waveguide via the molten salts.

In addition, the device may further include a widthwise driver for moving the optical waveguides in a perpendicular direction of a plane with respect to a moving direction of the lengthwise driver, or a vertical driver for vertically moving the optical waveguides.

Lower ends of the first and second optical waveguides may be cut to be inclined to 45°, first and second reflective mirrors having reflectivity of 99% or more may be installed at the cutout parts, respectively, and the first and second reflective mirrors may be disposed to oppose each other.

In addition, the first and second optical waveguides may be formed of a quartz material.

Preferably, the lengthwise driver comprises a sub screw and a sub guide rod spaced apart from each other and parallelly disposed between first and second sliders installed at both ends of the base disposed on the port, a sub slider disposed on the sub screw and the sub guide rod, and a sub motor for operating the sub screw, and the first optical waveguide is fixed to a first holder installed through the base, the second optical waveguide is fixed to a second holder formed through the sub slider, and the second optical waveguide passes through a through-hole formed in the base.

Preferably, the widthwise driver comprises a main screw and a main guide rod parallelly spaced apart from each other and installed at the first and second sliders, and a main motor for rotating the main screw to straightly move the base in a longitudinal direction of the main screw and the main guide rod.

Preferably, the vertical driver comprises a vertical screw vertically installed on any one of the first and second sliders to be driven by a vertical drive motor, a vertical guide rod vertically installed on any one of the first and second sliders, and a movable plate threadedly engaged with the vertical screw and mounted on the vertical guide rod to be vertically moved, and the movable plate has a first installation hole into which the first optical waveguide is inserted, and a second installation hole into which the second optical waveguide is inserted to be moved by the lengthwise driver.

According to the device for on-site measurement of concentration of uranium in high temperature molten salts of the present invention, different from a conventional method of collecting a sample using an off-line manner and analyzing the sample in a neighboring laboratory, concentration of uranium in molten salts can be on-site measured in a process field in real time. In addition, concentration of uranium 3+ and 4+ existing in the molten salts can be individually measured using a difference of absorption spectrum wavelength of uranium 3+ and 4+ compounds.

Further, an optimal spectrum can be secured by adjusting a distance between two optical waveguides according to a concentration range of uranium existing in molten salts. Furthermore, corrosion in the molten salts can be minimized by adjusting a height of the optical waveguide formed of a quartz material, and optimal analysis can be maintained by frequently exchanging the optical waveguide only.

BRIEF DESCRIPTION OF THE DRAWINGS

The above and other aspects, features and advantages of the present invention will become more apparent to those of ordinary skill in the art by describing in detail exemplary embodiments thereof with reference to the accompanying drawings, in which.

DETAILED DESCRIPTION

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

Figure 1:
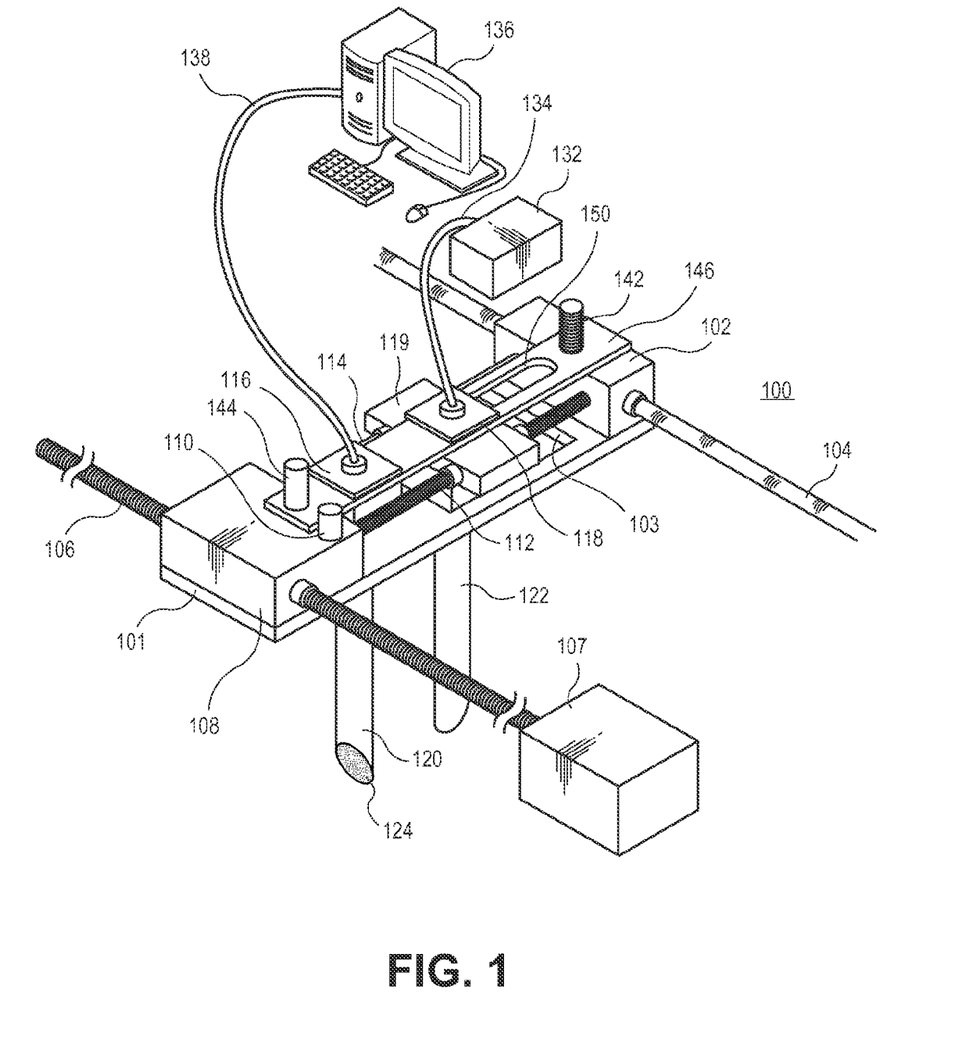
FIG. 1 is a schematic perspective view of a device for on-site measurement of concentration of uranium in high temperature molten salts in accordance with an embodiment of the present invention.
Figure 2:
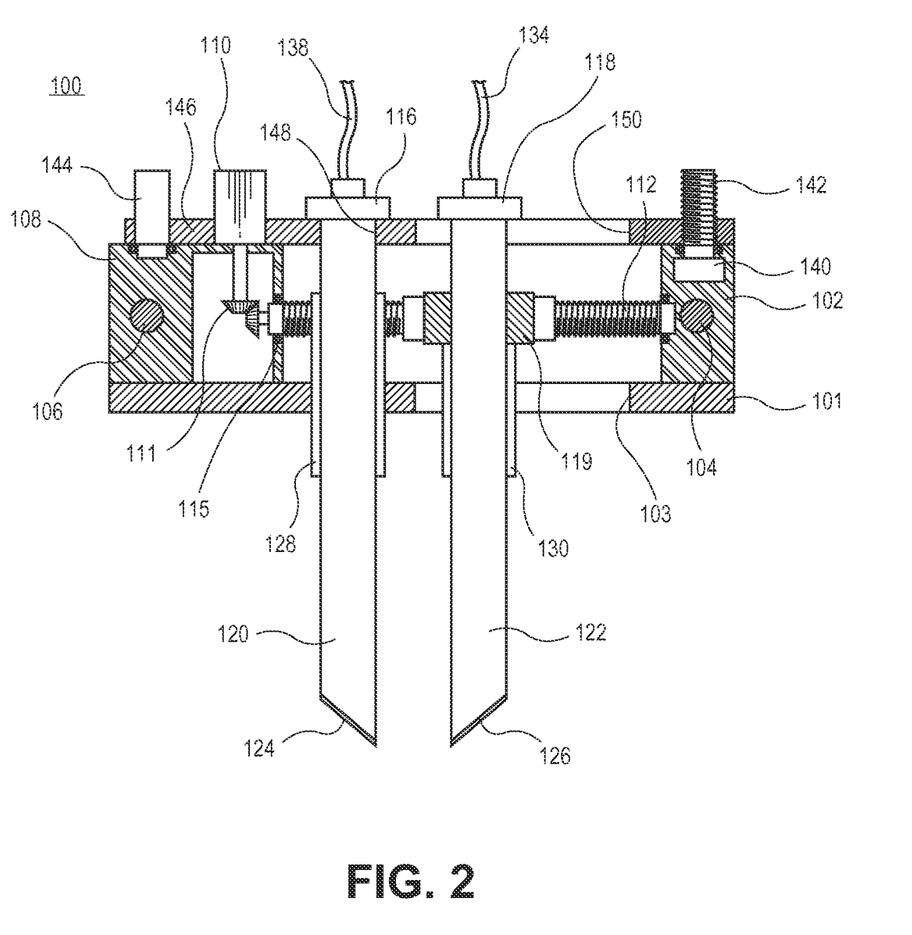
FIG. 2 is a cross-sectional view of the device for on-site measurement of concentration of uranium shown in FIG. 1.

FIG. 1 is a schematic perspective view of a device 100 for on-site measurement of concentration of uranium in high temperature molten salts in accordance with an exemplary embodiment of the present invention, and FIG. 2 is a cross-sectional view of the device 100 for on-site measurement of concentration of uranium.

The device 100 for on-site measurement of concentration of uranium includes first and second optical waveguides 120 and 122, a plane driver and a vertical driver for operating the two optical waveguides 120 and 122 in horizontal and vertical directions, a light source 132 for supplying light to the optical waveguides 120 and 122, and a spectrometer 136 for analyzing the light.

The optical waveguides 120 and 122 may use quartz cells or glass cells.

The first optical waveguide 120 is connected to the spectrometer 136 via a first cap 116 by a first optical cable 138 to transmit light, and the second optical waveguide 122 is connected to the light source 132 via a second cap 118 by a second optical cable 134 to transmit light.

A second reflective mirror 126 is installed at a lower end of the second optical waveguide 122 to reflect light from the light source 132 to supply the light toward the molten salts, and a first reflective mirror 124 is installed at a lower end of the first optical waveguide 122 to receive the light supplied from the second reflective mirror 126 of the second optical waveguide 122 and passed through the molten salts to transmit the light into the first optical waveguide 122. At this time, when the light generated from the light source 132 passes through the molten salts, the light remaining after absorption of some of the light must be transmitted to the spectrometer 136 at an optical transmission rate of 99% or more.

Therefore, the reflective mirrors 124 and 126 are formed by coating glass on lower end surfaces of the first and second optical waveguides 120 and 122 formed at an angle of 45°. In addition, it is preferable to check whether the reflective mirrors 124 and 126 are arranged well using a light source 132 before installation.

The plane driver includes a widthwise driver for straightly moving the first and second optical waveguides 120 and 122 together, and a lengthwise driver for adjusting a gap between the first and second optical waveguides 120 and 122.

The widthwise driver includes a main screw 106 and a main guide rod 104 parallelly spaced apart from each other, first and second sliders 108 and 102 fixed to both ends of a base 101 and installed at the main screw 106 and the main guide rod 104, respectively, and a main motor 107 for rotating the main screw 106 to straightly move the base 101 in a longitudinal direction of the main screw 106 and the main guide rod 104. Accordingly, the first slider 108 has a thread (not shown) formed therein and threadedly engaged with the main screw 106. The widthwise driver is not limited thereto but may be modified by a conventional art such as a hydraulic cylinder.

In addition, the lengthwise driver includes a sub screw 112 and a sub guide rod 114 parallelly disposed between the first and second sliders 108 and 102 and spaced apart from each other, and a sub slider 119 disposed on the sub screw 112 and the sub guide rod 114. Accordingly, the sub slider 119 has a thread (not shown) formed therein and threadedly engaged with the sub screw 112. In addition, the sub screw 112 is supported by a bearing 115 to support rotation thereof. Further, in order to transmit power of the sub motor 110 to the sub screw 112, a gear array 111 including a bevel gear, etc., may be provided. The lengthwise driver is not limited thereto but may be modified by a conventional art such as a hydraulic cylinder.

At this time, the first optical waveguide 120 is fixed to a first holder 128 installed through the base 101, and the second optical waveguide 122 is fixed to a second holder 130 formed through the sub slider 119 and passes through a through-hole 103 formed in the base 101. Accordingly, lower parts of the first and second optical waveguides 120 and 122 project downward beyond the base 101 to be submerged in the molten salts. It is preferable to adjust the first and second optical waveguides 120 and 122 to be submerged in the molted salts to a depth of 10 to 30 mm. Accordingly, the vertical driver for moving the widthwise driver in a vertical direction may be connected to the base 101 to vertically move the base 101, or connected to the main screw 106 and the main guide rod 104 to vertically move the main screw 106 and the main guide rod 104. The vertical driver may be configured using a rack and pinion driven by a motor, a hydraulic cylinder driven by a hydraulic pressure, and so on.

The vertical driver may be designed to adjust submerged portions of the first and second optical waveguides 120 and 122 according to a height of the molten salts when the device 100 for on-site measurement of concentration of uranium is mounted on a port formed at a pyroprocess apparatus (not shown), so that the optical waveguides 120 and 122 can be moved into the molten salts to measure the concentration only when analysis is needed.

In this embodiment, the vertical driver includes a vertical screw 142 vertically installed at any one of the first and second sliders 108 and 102 to be driven by a vertical drive motor 140, a vertical guide rod 144 vertically installed at any one of the first and second sliders 108 and 102, and a movable plate 146 threadedly engaged with the vertical screw 142 and mounted on the vertical guide rod 144 to be vertically moved.

The movable plate 146 has a first installation hole 148 in which the first optical waveguide 120 is inserted, and a second installation hole 150, elongated in a longitudinal direction, through which the second optical waveguide 122 is inserted to be moved by the lengthwise driver.

Therefore, when the vertical drive motor 140 is driven in one direction to move the movable plate 146 upward by threaded engagement with the vertical screw 142, the first and second optical waveguides 120 and 122 installed in the first and second installation holes 148 and 150 formed in the movable plate 146 by the first and second caps 116 and 118 are raised. At this time, since the second installation hole 150 is a slit having an elongated circular shape or a rectangular shape, a gap between the first and second waveguides 120 and 122 can be varied according to operation of the lengthwise driver.

On the other hand, when the vertical drive motor 140 is driven in an opposite direction, the movable plate 146 is lowered to move the first and second optical waveguides 120 and 122 downward. Accordingly, it is possible to precisely control the first and second optical waveguides 120 and 122 in a vertical direction through an operation of the vertical drive motor 140 only.

The through-hole 103 is elongated in a moving direction of the sub slider 119 so that the second optical waveguide 122 can move in the through-hole 103 according to movement of the sub slider 119. In addition, as the second optical waveguide 122 moves, a gap between the first and second optical waveguides 120 and 122 can be adjusted. At this time, the gap between the first and second optical waveguides 120 and 122 may be adjusted to 1 to 20 mm according to a concentration range of uranium in the molten salts.

Further, when corrosion due to the molten salts occurs to reduce an optical transmission rate, the optical waveguides 120 and 122 may be attached or detached to/from the first and second holders 128 and 130 to maximize precision of concentration measurement of the uranium according to circumstances.

Figure 3:
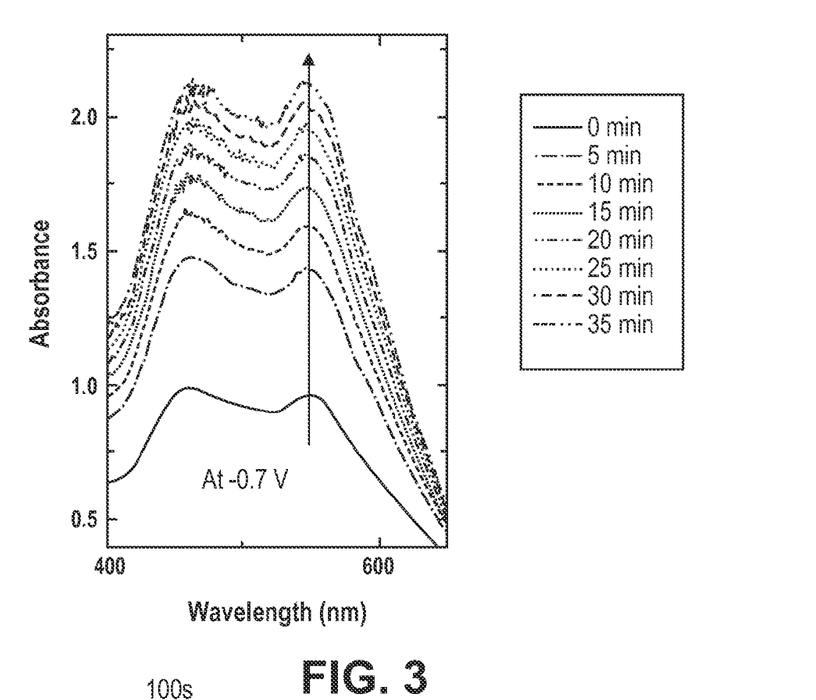
FIG. 3 is a graph showing an absorption spectrum of uranium according to a time when an electrochemical potential in accordance with an exemplary embodiment of the present invention is applied to −0.7V.
Figure 4:
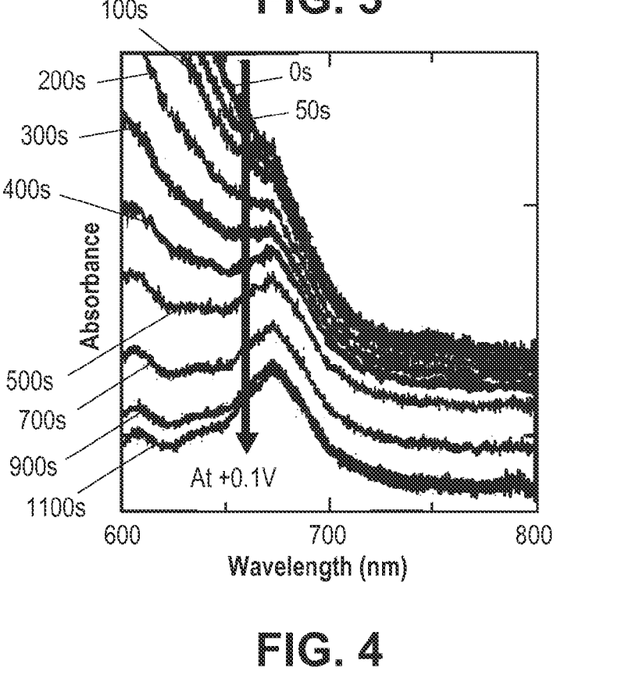
FIG. 4 is a graph showing an absorption spectrum of uranium according to a time when an electrochemical potential in accordance with an exemplary embodiment of the present invention is applied to +0.1V.

FIGS. 3 and 4 represent absorption spectrum of uranium 3+ and 4+. The uranium 3+ represents strong absorbance at a wavelength range of 400 to 600 nm, and the uranium 4+ represents weaker absorbance at a wavelength range of 500 to 700 nm than that of the uranium 3+.

Specifically, FIG. 3 shows variation in absorption spectrum of uranium according to a time when a potential is applied to −0.7V. In the wavelength range of 400 to 600 nm, an absorption peak of uranium 3+ is increased in an arrow direction. That is, uranium 4+ ions melted in the molten salts are reduced into uranium 3+ ions by an electrode reaction so that uranium 3+ ions in the molten salts are increased to gradually increase an absorption spectrum of uranium 3+.

FIG. 4 shows variation in absorption spectrum of uranium according to a time when a potential is applied to +0.1 V. A typical optical absorption peak of uranium 4+ having a wavelength of 660 nm is increased in an arrow direction. As a result of a reaction in which the uranium 3+ ions melted in the molten salts are oxidized to uranium 4+ ions, uranium 3+ ions in the molten salts are gradually disappeared due to an electrode reaction to reduce an absorption peak of uranium 3+, and a content of uranium 4+ is increased so that a peak in a 500 to 700 nm region, more specifically, a peak at 660 nm as a peak of uranium 4+ is increased.

Figure 5:
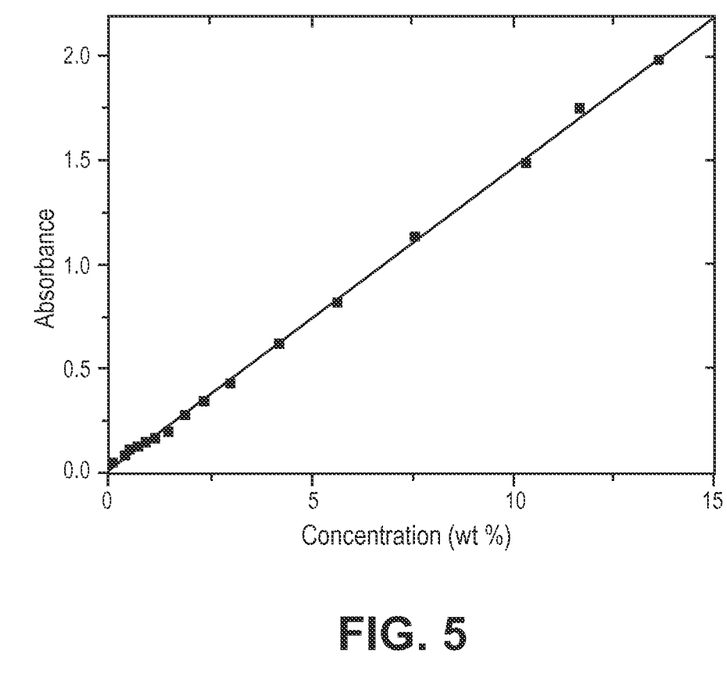
FIG. 5 is a graph showing a variation in absorption according to concentration of uranium in accordance with an embodiment of the present invention.

Here, FIG. 5 shows variation in optical absorbance at a wavelength of 450.5 nm according to concentration of uranium 3+ compound. As shown in FIG. 5, it will be appreciated that optical absorbance directly ($R^2=0.9989$) varies depending on variation in concentration of uranium compound.

Accordingly, it is possible to precisely measure concentration of uranium through measurement of optical absorbance of uranium spectrum.

Such absorption spectrum can be checked by performing an absorption spectrum measurement test in real time simultaneously with an electrochemical reaction test for adjusting an oxidation number by electrochemically applying a potential as described in the following experimental example.

EXPERIMENTAL EXAMPLE

Hereinafter, an experimental device for electrochemical oxidation reduction reaction is manufactured, and an electrochemical oxidation reduction reaction and absorption spectrum test of uranium compound is performed.

Figure 6:
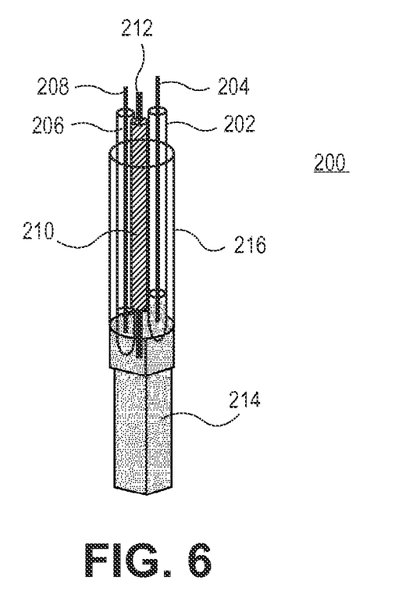
FIG. 6 is a schematic perspective view for explaining an experimental device for electrochemical oxidation reduction reaction in accordance with an embodiment of the present invention.

FIG. 6 is a schematic view of an experimental device for electrochemical oxidation reduction reaction 200.

Referring to FIG. 6, the experimental device for oxidation reduction reaction 200 is a three-electrode system including a working electrode 212, a reference electrode 208 and a counter electrode 204, for performing an electrochemical oxidation reduction reaction in an absorption spectrum cell 216, which are submerged in an upper part of high temperature molted salts 214 in the spectrum measurement cell. The working electrode 212 is installed at a spacing member 210, and the spacing member 210 electrically insulates the reference electrode 208 and the counter electrode 204 from each other.

Figure 7:
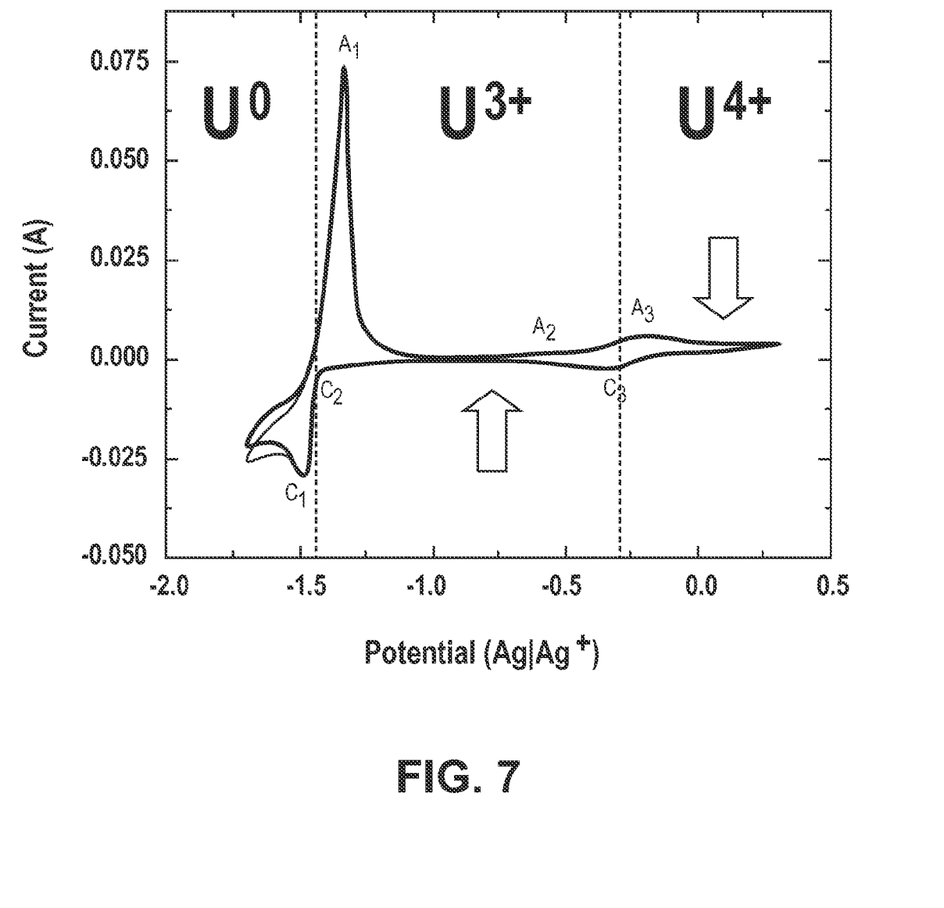
FIG. 7 is a graph showing circulation voltage current curves of uranium in molten salts for explaining electrochemical oxidation reduction treatment in accordance with an embodiment of the present invention.

FIG. 7 shows cyclic voltammogram of uranium obtained using the experimental device for oxidation reduction reaction 200.

According to the cyclic voltammogram, uranium ions cause an oxidation reduction reaction of 3+ and 4+ at a region of −0.3 V. When a potential of 0.3V or less is applied to the working electrode 100, uranium 3+ ions are generated, and when a potential of −0.3V or more is applied, uranium 4+ ions are obtained. Accordingly, as shown in FIGS. 3 and 4, potentials of −0.7V and +0.1V are applied to the molten salts including uranium.

The many features and advantages of the invention are apparent from the detailed specification, and, thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and, accordingly, all suitable modifications and equivalents may be resorted to that fall within the scope of the invention.

What is claimed is:

1. A device for on-site measurement of concentration of uranium in high temperature molten salts comprising:
   first and second optical waveguides submerged in molten salts including uranium through a port formed at an upper side of a pyrochemical process apparatus;
   a lengthwise driver installed at the port to be operated to adjust a distance between the optical waveguides;
   a light source for supplying light to the second optical waveguide; and
   a spectrometer connected to the first optical waveguide to analyze the light emitted from the second optical waveguide and introduced through the first optical waveguide via the molten salts.

2. The device according to claim 1, wherein lower ends of the first and second optical waveguides are cut to be inclined at 45°, first and second reflective mirrors are installed at the cutout parts, respectively, and the first and second reflective mirrors are disposed to oppose each other.

3. The device according to claim 1, wherein the first and second optical waveguides are formed of a quartz material.

4. The device according to claim 1, wherein:
   the lengthwise driver comprises a sub screw and a sub guide rod spaced apart from each other and parallelly disposed between first and second sliders installed at both ends of the base disposed on the port, a sub slider disposed on the sub screw and the sub guide rod, and a sub motor for operating the sub screw, and
   the first optical waveguide is fixed to a first holder installed through the base, the second optical waveguide is fixed to a second holder formed through the sub slider, and the second optical waveguide passes through a through-hole formed in the base.

5. A device for on-site measurement of concentration of uranium in high temperature molten salts comprising:
   first and second optical waveguides submerged in molten salts including uranium through a port formed at an upper side of a pyrochemical process apparatus;
   a lengthwise driver installed at the port to be operated to adjust a distance between the optical waveguides;
   a widthwise driver for moving the optical waveguides in a perpendicular direction of a plane with respect to a moving direction of the lengthwise driver;
   a light source for supplying light to the second optical waveguide; and
   a spectrometer connected to the first optical waveguide to analyze the light emitted from the second optical waveguide and introduced through the first optical waveguide via the molten salts.

6. The device according to claim 5, wherein lower ends of the first and second optical waveguides are cut to be inclined at 45°, first and second reflective mirrors are installed at the cutout parts, respectively, and the first and second reflective mirrors are disposed to oppose each other.

7. The device according to claim 5, wherein the first and second optical waveguides are formed of a quartz material.

8. The device according to claim 5, wherein:
   the lengthwise driver comprises a sub screw and a sub guide rod spaced apart from each other and parallelly disposed between first and second sliders installed at both ends of the base disposed on the port, a sub slider disposed on the sub screw and the sub guide rod, and a sub motor for operating the sub screw,
   the first optical waveguide is fixed to a first holder installed through the base, the second optical waveguide is fixed to a second holder formed through the sub slider, and the second optical waveguide passes through a through-hole formed in the base, and
   the widthwise driver comprises a main screw and a main guide rod parallelly spaced apart from each other and installed at the first and second sliders, and a main motor for rotating the main screw to straightly move the base in a longitudinal direction of the main screw and the main guide rod.

9. A device for on-site measurement of concentration of uranium in high temperature molten salts comprising:
   first and second optical waveguides submerged in molten salts including uranium through a port formed at an upper side of a pyrochemical process apparatus;
   a lengthwise driver installed at the port to be operated to adjust a distance between the optical waveguides;
   a vertical driver for vertically moving the optical waveguides;
   a light source for supplying light to the second optical; and a spectrometer connected to the first optical waveguide to analyze the light emitted from the second optical waveguide and introduced through the first optical waveguide via the molten salts.

10. The device according to claim 9, wherein lower ends of the first and second optical waveguides are cut to be inclined at 45°, first and second reflective mirrors are installed at the cutout parts, respectively, and the first and second reflective mirrors are disposed to oppose each other.

11. The device according to claim 9, wherein the first and second optical waveguides are formed of a quartz material.

12. The device according to claim 9, wherein:
the lengthwise driver comprises a sub screw and a sub guide rod spaced apart from each other and parallelly disposed between first and second sliders installed at both ends of the base disposed on the port, a sub slider disposed on the sub screw and the sub guide rod, and a sub motor for operating the sub screw, the first optical waveguide is fixed to a first holder installed through the base, the second optical waveguide is fixed to a second holder formed through the sub slider, and the second optical waveguide passes through a through-hole formed in the base, the vertical driver comprises a vertical screw vertically installed on any one of the first and second sliders to be driven by a vertical drive motor, a vertical guide rod vertically installed on any one of the first and second sliders, and a movable plate threadedly engaged with the vertical screw and mounted on the vertical guide rod to be vertically moved, and the movable plate has a first installation hole into which the first optical waveguide is inserted, and a second installation hole into which the second optical waveguide is inserted to be moved by the lengthwise driver.

* * * * *